United States Patent [19]

Keil et al.

[11] Patent Number: 4,686,243

[45] Date of Patent: Aug. 11, 1987

[54] COPOLYMER, A PROCESS FOR ITS PREPARATION AND ITS USE AS ENZYME SUPPORTS

[75] Inventors: Karl-Heinz Keil, Hanau; Dieter Wullbrandt, Hofheim am Taunus; Reinhold Keller, Bad Soden am Taunus; Friedrich Engelhardt, Frankfurt am Main, all of Fed. Rep. of Germany

[73] Assignee: Hoechst Aktiengesellschaft, Fed. Rep. of Germany

[21] Appl. No.: 919,678

[22] Filed: Oct. 16, 1986

[30] Foreign Application Priority Data

Oct. 19, 1985 [DE] Fed. Rep. of Germany ....... 3537259

[51] Int. Cl.$^4$ ................................................ C08J 9/00
[52] U.S. Cl. ...................................... 521/149; 521/56; 521/150; 526/258; 526/266; 435/180; 435/181; 435/182
[58] Field of Search .......................... 521/56, 149, 150

[56] References Cited

U.S. PATENT DOCUMENTS

| | | | |
|---|---|---|---|
| 4,551,482 | 11/1985 | Tschang et al. | 521/149 |
| 4,568,706 | 2/1986 | Noetzel et al. | 521/149 |
| 4,582,860 | 4/1986 | Begwood et al. | 521/149 |
| 4,611,014 | 9/1986 | James et al. | 521/149 |

*Primary Examiner*—Morton Foelak
*Attorney, Agent, or Firm*—Finnegan, Henderson, Farabow, Garrett and Dunner

[57] ABSTRACT

A porous, bead-like copolymer which can be employed to excellent effect for the fixation of enzymes is obtained by suspension polymerization of monomeric oxiranylalkyl compounds and/or 2-aziridinylalkyl compounds, n-valent crosslinking agents, N-vinylamides, heterocyclic 5-membered ring compounds or 6-membered ring compounds, having a polymerizable olefinic group in each case, and polymerizable quaternary ammonium salts.

4 Claims, No Drawings

COPOLYMER, A PROCESS FOR ITS PREPARATION AND ITS USE AS ENZYME SUPPORTS

Enzymes bound to supports have a number of applications, for example in medical analysis in the preparation of pharmaceutical and plant-protection products, and in the preparation of foodstuffs. The advantages of using immobilized enzymes lie in their simple separation from the substrate or from reaction products, their frequently increases stability compared to the soluble form, their reusability, and the possibility of carrying out continuous reactions in columns or similar reactors.

A number of methods for the immobilization of enzymes are known. A detailed survey is given, for example, in Methods in Enzymology, Vol. XLIV, "Immobilized Enzymes", (Academic Press, 1976) and in J. Chibata: Immobilized Enzymes (Kodansha Ltd., John Wiley & Sons, 1978). One frequently described route is the absorptive, ionic or covalent bonding of enzymes to supports.

German Published Specification No. 2,237,316 describes swellable, crosslinked bead polymers, obtained by copolymerization of monomers, crosslinking monomers and hydrophilic monomers containing reactive groups, for use as support substances. The haloalkyl, epoxide, carboxyl chloride, carboxyl anhydride, carboxyl azide, phenyl carboxylate and hydroxamic groups are published therein as reactive groups. However, these support materials have a number of disadvantages; thus, in the case of several of them, enzyme fixation is rather protracted; their activity, in some cases, is unsatisfactory, and, in addition, charges are incorporated when anhydride versions are used.

German Published Specification No. 2,722,751 and European Patent Application No. 0,129,719 describe the preparation of bead polymers based on (meth)acrylamide derivatives for enzyme fixation. However, these products display excessive excessive hydrophobia toward the hydrophilic enzyme systems, so the fixation only proceeds unsatisfactorily.

It has now been found that, by incorporating quaternary nitrogen atoms during the polymerization, the copolymer according to the invention has a high selectivity towards enzyme systems.

The invention therefore relates to:

(1) A crosslinked, porous, bead-like copolymer having
(a) repeating units of the compound of the general formula I,

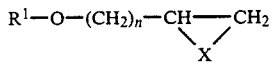

in which
R$^1$ denotes (C$_2$–C$_4$) alkenyl or the corresponding acid,
X denotes oxygen or NH, and
n denotes 1–6,
or repeating units of the compound of the general formula II,

in which
R$^2$ and R$^3$, independently of one another, denote hydrogen or methyl,
or several such compounds,
(b) repeating units of one or more n-valent crosslinking agents,
(c) repeating units of the compound of the general formula III $$CH_2=CH-N(R^4)-C(R^5)=O \qquad III$$

in which
R$^4$ and R$^5$, independently of one another, denote hydrogen or (C$_1$–C$_3$)-alkyl, or, together, represent —(CH$_2$)$_n$— where n=3, 4 or 5,
or several such compounds,
(d) repeating units of the compounds of the general formula IV,

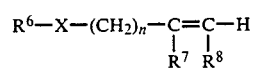

in which
R$^6$ denotes the radical of a heterocyclic 5-membered ring compound which has at least one protonatable nitrogen atom in the ring, or pyridyl, quinolyl, isoquinolyl or pyrazinyl,
R$^7$ and R$^8$ denote hydrogen or (C$_1$–C$_4$)-alkyl,
X denotes oxygen or sulfur or a direct bond, and n denotes a number from 0 to 4,
or several such compounds,
(e) repeating units of the compound of the general formula V

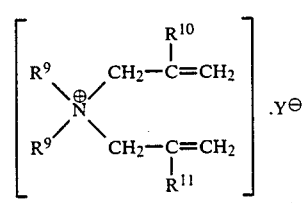

in which
R$^9$ denotes a (C$_1$–C$_{10}$)-alkyl group,
R$^{10}$ and R$^{11}$, independently of one another, denote hydrogen or methyl and
Y denotes halogen,
or several such compounds.

(2) A process for the preparation of the crosslinked, porous, bead-like copolymers according to the invention, wherein the compounds mentioned under 1 a-e are polymerized by reverse-phase suspension polymerization.

(3) The use of crosslinked, porous, bead-like copolymers according to the invention as enzyme supports.

The copolymer according to the invention is composed of 5 monomer groups, which are designated below as group A to group E. The polymer is composed of repeating units of these monomers. Units here is taken to means groups of the monomers which are randomly distributed in the copolymer. Both an oxiranylalkyl compound and a 2-aziridinylalkyl compound having an alkyl group containing up to 6 carbon atoms can be employed as monomers from the group A having the general formula I, a chain length of 1 to 4 carbon atoms being preferred. The oxiranylalkyl radical or the 2-aziridinylalkyl radical is bonded, via an oxygen atom, to an alkenyl group having up to 4 carbon atoms. Glycidyl acrylate, glycidyl methacrylate, allyl glycidyl ether and methallyl glycidyl ether or dihydromyrcene oxide are employed preferably. Preferred monomers of the general formula II, likewise allocated to group A, are vinylcyclohexene monooxide and limonene oxide.

The monomers of group B have the function of crosslinking agents during the preparation of the copolymers according to the invention. They link n-polymer chains together, n being a number greater than or equal to 2. In particular, $n=2, 3, 4$, and preferably 2.

Suitable crosslinking agents are, for example, compounds which contain n-polymerizable radicals, particularly of the formulae $CH_2=CH-$, $CH_2=CH-CH_2-$, $CH_2=CH(R^{12})-CO-$ or $CH_2=CH(R^{12})-CO-O$ in the molecule, n having the above-mentioned meaning, normally 2, 3 or 4, preferably 2, and $R^{12}$ denoting hydrogen or $(C_1-C_4)$-alkyl, particularly hydrogen or methyl. Examples of such compounds are: trialkyl cyanurate, triallyl phosphate, N,N',N''-trisacryloylperhydrotriazine, 1,2,3-trivinyloxypropane, tetraallyloxyethane, pentaallylsucrose, triallylamine, N,N',N''-tris-(2-acryloyloxyethyl- or -methacryloyloxyethyl) isocyanurate, diallyl ethenephosphonate, ethylene glycol 1,2-bis-(ethenephosphonate), and furthermore general compounds of the formulae VI, VII or VIII

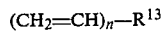   VI

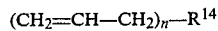   VII

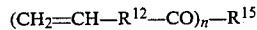   VIII in which $R^{12}$ has the abovementioned meaning, n normally denotes 2, 3 or 4, preferably 2, and $R^{14}$ represents the radical, produced by removal of n acidic H atoms, of a di-, tri-, tetra- or polycarboxylic acid, $R^{15}$ represents the radical, produced by removal of n of a di-, tri-, tetra- or polyol and $R^{13}$ represents the radical, produced by removal of n hydrogen atoms, of an aliphatic, aromatic or heteroaromatic hydrocarbon.

Suitable crosslinking agents of the formula VI are divinylbenzenes, particularly 1,4-divinylbenzene, trivinylbenzenes, divinylpyridines and divinylquinolines.

Examples of suitable crosslinking agents of the formula VII are triallyl tricarballylate, triallyl aconitate, triallyl citrate, triallyl trimesinate, triallyl trimellitate, diallyl oxalate, divinyl phthalate, diallyl maleate, diallyl fumarate, diallyl adipate and diallyl phthalate.

Examples of suitable crosslinking agents of the formula VIII are trimethylolpropane triacrylate and methacrylate, pentaerythrite tetraacrylate and tetramethacrylate, pentaerythrite triacrylate and timethacrylate, dimethylene glycol diacrylate or dimethacrylate, and butylene glycol diacrylate or dimethacrylate.

Of the compounds of the general formula VIII, the diacrylates and, in particular, the dimethylacrylates of ethylene glycol, diethylene glycol and polyethylene glycols 200 to 600, particularly the dimethacrylates of polyethylene glycols 200 to 600, are particularly suitable.

Suitable crosslinking agents are furthermore, for example, diallylamine, divinyl ketone, divinyl sulfone and diallylmelamine.

Divalent crosslinking agents and water-soluble crosslinking agents are preferred. Suitable water-soluble crosslinking agents are, in particular, derivatives of acrylic or methacrylic acid, such as, for example, N,N'-methylenebisacrylamide, N,N'-methylenebismethacrylamide, N,N'-methylenebis(N-hydroxymethylmethacrylamide), N,N'-bis(methacryloyl)aminoacetic acid, N,N'-bis(acryloyl)aminoacetic acid, 1,2-bis(acrylamido)-1,2-dihydroxyethane, 1,2-bis(methacrylamido)-1,2-dihydroxyethane, 1,2-bis(N-hydroxymethylmethacrylamido)-1,2-dihydroxyethane, 1,2-bis(N-methoxymethylmethacrylamido)-1,2-dimethyloxyethane, 1,6-bis(acrylamido)hexane, 1,6-bis-(methacrylamido)hexane, 2-methyl-1,4-bis(acrylamido)butane ("isovalerylidenebisacrylamide"), 2-methyl-1,4-bis(methacrylamido)butane ("isovalerylidenebismethacrylamide"), the diacrylates and dimethacrylates of ethylene glycol, diethylene glycol and the polyglycols 200 to 600.

Combinations of two or more crosslinking agents, for example of N,N'-methylenebisacrylamide/N,N'-bis(acryloyl)aminoacetic acid; N,N'-methylenebisacrylamide/isovalerylidenebisacrylamide; N,N'-methylenebisacrylamide/ethylene glycol 1,2-bis(ethenephosphonate), are also favorable. Preferred crosslinking agent combinations can contain, as one crosslinking agent component, not only N,N'-methylenebisacrylamide and/or N,N'-methylenebismethacrylamide, but also the diacrylates and/or dimethacrylates of ethylene glycol, diethylene glycol or the polyethylene glycols 200 to 600, or N,N',N''-tris(2-acryloyloxyethyl)isocyanurate or N,N',N''-tris(2-methacryloyloxyethyl)isocyanurate. Particularly preferred crosslinking agent combinations contain or comprise N,N'-methylenebisacrylamide/dimethyacrylate of polyethylene glycol 200 to 600 and/or the corresponding methacrylamide and/or the corresponding diacrylate.

However, suitable n-valent crosslinking agents are also polymerizable silicon or organoboron compounds, particularly those compounds which only contain one or two polymerizable olefinic double bonds in the molecule, but which can additionally link $(n-1)$ or $(n-2)$ polymer chains to one another because of secondary reactions. Such crosslinking agents are, for example, alkoxy group-containing silanes in which the alkoxy groups are hydrolyzed in aqueous medium to form intermediate Si—OH groups. Two such silanol groups then cause the linking of two chains, with condensation and formation of a siloxane bond Si—O—Si. Suitable such crosslinking agents are organosilicon compounds, as long as they contain 1 or 2 olefinic double bonds and $(n-1)$ or $(n-2)$ alkoxy groups. Of the polymerizable organosilicon or organoboron compounds, the polymerizable organosilicon compounds are preferred. Suitable polymerizable organosilicon compounds are, for example, polymerizable olefinic group-containing silanes, siloxanes and silazanes. 3-(Trimethoxysilyl)propyl acrylate or methacrylate, 3-(triethoxysilyl)propyl acrylate or methacrylate, 3-(tri(methoxyethoxy)silyl)-propyl acrylate or methacrylate, 3-(tri(methoxyethoxyethoxy)silyl)propyl acrylate or methacrylate, 3-(di-(methoxy)methylsilyl)propyl acrylate or methacrylate, 3-(di-(ethoxy)ethylsilyl)propyl acrylate or methacrylate, vinyltriethoxysilane, vinyltrimethoxysilane, vinyltrimethoxysilane, vinyltriallyloxysilane, allyltriallyloxysilane, vinylmethyldiethoxysilane, vinylmethyldimethoxysilane, vinyltriacetoxysilane, vinyltri(methoxyethoxy)silane, 1,3-divinyl-1,1,3,3-tetramethyldisiloxane, 1,3-divinyl-1,1,3,3-tetramethyldisilazane,
$C_2=CH-COO-(CH_2)_3-[Si(CH_3)_2-O]_p-Si(CH_3)_2-(CH_2)_3-O-CO-CH=CH_2$,
$CH_2=C(CH_3)-COO-(CH_2)_3-[Si(CH_3)_2-O]_p-Si(CH_3)_2-(CH_2)_3-O-CO-C(CH_3)=CH_2$,
where p denotes a number from 1 to 20, particularly a number from 1 to 10, and $CH_2=CH-CH_2-NH-SiH(CH_3)-N(CH_2CH=CH_2)-SiH(CH_3)N-H-CH_2-CH=CH_2$.

Suitable organoboron compounds are, for example, triallyl borate and trimethylally borate.

The monomers of group C are vinylamides of the general formula III.

Suitable N-vinylamides are, for example, N-vinylformamide, N-vinylacetamide, N-vinyl-N-methylacetamide, N-vinyl-N-methylformamide, N-vinyl-N-ethylacetamide, N-vinylpropionamide, N-vinyl-N-methylpropionamide, N-vinylethylpropionamide, N-vinylbutyramide, N-vinyl-N-methylbutyramide, N-vinyl-N-ethylbutyramide, N-vinylpyrrolidone and N-vinylcaprolactam. N-vinylformamide and, in particular, N-vinyl-N-methylacetamide are particularly suitable.

The monomers of group D are heterocyclic 5-membered ring compounds or 6-membered ring compounds, such as pyridyl, quinolyl, isoquinolyl or pyrazinyl compounds, having a polymerizable olefinic group in each case, as represented in the general formula IV.

As a rule, the polymerizable olefinic group is directly, but also, if appropriate, indirectly, for example via an oxygen or sulfur atom, bonded to the nucleus. The combination $H/CH_3$ or $CH_3/H$ or $H/H$ is preferred for the radicals $R^7$ and $R^8$. For n, 1, but particularly 0, is preferred. Polymerizable olefinic groups are, in particular, the vinyl, allyl, methallyl or isopropanyl groups. If $R^6$ represents the radical of a heterocyclic 5-membered compound, then this can have, for example, one, two, three or four nitrogen atoms, of which at least one must be protonatable, the heterocyclic ring, if appropriate, optionally also containing a further heteroatom or several other heteroatoms, in particular oxygen and/or sulfur. Protonatable nitrogen atoms are basic nitrogen atoms, having a free electron pair, which are incorporated, for example, in the 5-membered ring as —N=, —NH— or —N—. Nitrogen atoms which are adjacent, for example, to a keto group no longer have basic properties and can thus no longer be protonated. The heterocyclic 5-membered ring can be saturated, partially saturated or unsaturated, can represent an imidazole, imidazoline, oxazole, oxazoline, oxazolidine, thiazole, oxadiazole, pyrrole, triazole or tetrazole, and can have, if appropriate, one or more further $(C_1-C_4)$-alkyl and/or $(C_2-C_4)$-hydroxyalkyl groups.

The following, for example, may be mentioned as a heterocyclic 5-membered ring compound which contains a polymerizabel olefinic group and which has at least one protonatable nitrogen atom in the ring: 1-vinyl-1,2,3-triazole, 1-vinyl-1,2,4-triazole, 4-vinyl-1,2,3-triazole, 5-vinyl-1,2,3-triazole, 1-vinyl-1,2,3,4-tetrazole, 2-vinyl-1,2,3,4-tetrazole, 2-allyl-1,2,3,4-tetrazole, 1-allyl-1,2,3,4-tetrazole, 1-methyl-5-vinyl-1,2,3,4-tetrazole, 2-methyl-5-vinyl-1,2,3,4-tetrazole, 3-vinyl-1,2,4-oxadiazole, 3-vinyl-5-methyl-1,2,4-oxadiazole, 3-isopropenyl-1,2,4-oxadiazole, 2-isopropenyl-1,3,4-oxadiazolin-5-one, 3-isopropenyl-1,2,4-oxadiazole, 3-isopropenyl-5-methyl-1,2,4-oxadiazole, 2-vinyloxazoline, 2-isopropenyloxazoline, 2-vinyl-3-methyloxazolidine, 2-vinylthiazole, 4-vinylthiazole, 1-vinyl-2-imidazoline, 2-vinyl-4-(or 5-)methyl-2-imidazoline, 1-vinyl-2-methyl-2-imidazoline, 1-vinylimidazole, 1-methyl-2-vinylimidazole, 1-vinyl-2-methylimidazole, 1-vinyl-4-(2-hydroxyethyl)imidazole, N-vinylpyrrole, 2-isopropenyl-2-imidazoline, 2-vinyl-3-methyl-2-imidazoline and 1-vinyl-2,4-di-methylimixazole. The vinylimidazoles, particularly 1-N-vinylimidazole, are preferred.

If $R^6$ represents the radical or a pyridyl, quinolyl, isoquinolyl or pyrazinyl compound, then it has, if it contains further substitutents, in particular one, two or three $(C_1-C_4)$alkyl and/or OH substituents. One or two alkyl radicals, an OH group, or an OH group and an alkyl radical are particularly preferred as substituents.

Suitable compounds of a pyridyl, quinolyl, isoquinolyl or pyrazinyl compound containing a polymerizable olefinic group, are for example: 2-vinylpyridine, 3-vinylpyridine, 4-vinylpyridine, 3-isopropenylpyridine, 2-vinyl-5-methylpyridine, 2-methyl-5-vinylpyridine, 3-methyl-5-vinylpyridine, 2,4-dimethyl-6-vinylpyridine, 3-methyl-4-vinylpyridine, 3-ethyl-4-vinylpyridine, 3-methyl-2-vinylpyridine, 3-ethyl-2-vinylpyridine, 4-methyl-4-vinylquinoline, 2-methyl-5-vinylquinoline, 1-methyl-5-vinylisoquinoline, 2-isopropenylquinoline, 2-vinylpyrazine, 2-vinyl-5-ethylpyridine, 2-vinyl-4,6-dimethylpyridine, 2-vinylquinoline and 2-methyl-3-vinyl-8-hydroxyquinoline. Of the pyridyl, quinolyl, isoquinolyl or pyrazinyl compounds, the pyridyl compounds, particularly compounds of vinylpyridines, above all 4-vinylpyridine, are preferrred.

The monomers of group E are polymerizable quaternary ammonium salts of the general formula V. Preferred compounds are those in which $R^9$ represents a $(C_1-C_5)$-alkyl group. The following compounds are particularly preferred: diallyldimethyammonium chloride, diallydiethylammonium chloride, diallyldi-n-propylammonium chloride, diallyldi-tertiarybutylammonium chloride, diallyldi-n-butylammonium chloride, diallyldi-n-pentylammonium chloride and diallyldiisopentylammonium chloride.

The crosslinked, porous, bead-like copolymers according to the invention are prepared by bead polymerization of 10–50% by weight, preferably 25–75% by weight, of monomer component A (compound of the general formula I or II), 0.05–50% by weight, preferably 0.1–35% by weight, of monomer component B (n-valent crosslinking agent), 0–50% by weight, preferably 5–25% by weight, of monomer component C (compound of the general formula III), 0–90% by weight, preferably 10–80% by weight, of monomer component D (compound of the general formula IV) and 95–80% by weight, preferably 10–50% by weight, of monomer component E (compound of the general formula V). In the copolymerization, up to 50% by weight of the pyridyl, quinolyl, isoquinolyl or pyrazinyl compound employed can be replaced by one or more of the abovementioned heterocyclic 5-membered ring compounds having one polymerizable olefinic group and at least one protonatable nitrogen atom. The polymerizable monomers can be employed, as a rule, in commercially available form, i.e. without previous purification.

The copolymerization is carried out by the bead polymerization process (cf., for example, Houben-Weyl: Methoden der organischen Chemie ]Methods of Organic Chemitry], 4th edition, volume 14, 1 (1961), Makromolekulare Stoffe [Macromolecular Substances], part 1, page 406 et. seq.). In the bead polymerization, the monomer mixture to be polymerized is, as a rule, dispersed to the desired bead size in water or another liquid in which the monomers and the copolymer produced are insoluble, by mechanical stirring or shaking, preferably under concomitant action of one or more suitable dispersing agents, and is subsequently copolymerized. The copolymerization is initiated in a fashion which is known per se, for example by the action of UV light or high-energy radiation, but as a rule by an initiator which is soluble in the monomer mixture and which supplies free radicals. Suitable initiators are, for example, benzoyl peroxide, tert-butyl hydroperoxide, cumene peroxide, methyl ethyl ketone peroxide, lauroyl peroxide, tert-butyl perbenzoate, tert-butyl diperphthalate, azodiisobutyronitrile, 2,2'-azobis(2,4-dimethylvaleronitrile), 2-phenylazo-2,4-dimethyl-4-methoxyvaleronitrile, 2-cyano-2-propylazoformamide, azodiisobutyramide, and dimethyl, diethyl or dibutyl azobismethylvalerate. About 0.01 to 2% by weight, preferably 0.1 to 1% by weight, of initiator are used, based on the amount of monomer (including crosslinking agent).

As dispersing agent, water-soluble or water-solubilized natural products, particularly carbohydrates and albumens, for example solubilized starch, methyl starch, methyl cellulose or other cellulose ethers, methylhydroxypropyl cellulose, cellulose glycolate, and furthermore cholesterol, saponin, adhesive, tragacanth gum, etc. or water-soluble high molecular weight synthetic emulsifiers, such as, for example, polyvinyl alcohol, polyacrylates or polymethacrylates, in amounts from 0.05 to 3% by weight, preferably 0.1 to 1% by weight, based on the amount of water present, are used.

It is expedient to carry out the bead polymerization in the presence of salts, such as, for example, sodium chloride or sodium nitrite, particularly sodium formate, which are dissolved in the aqueous phase. It is furthermore expedient to carry out the polymerization with the exclusion of oxygen. This can occur, for example, in a known fashion by flushing with or passing through an inert gas, such as, for example, nitrogen. The bead polymerization is normally carried out at temperatures from 45° to 95° C., preferably from 55° to 85° C., and is, as a rule, complete after 0.3 to 3 hours. After the polymerization is complete, the bead-like copolymer obtained is separated off, washed with water or an organic solvent, and dried.

The crosslinked copolymer according to the invention is present in the form of porous beads whose diameter can be selected, by means of the selection of the preparation conditions, in the range from about 2 to 0.04 mm. Under the given preparation conditions, beads are obtained having a narrow diameter range. The copolymer according to the invention is present, in particular, in the form of beads having a diameter of 0.02 to 0.2 mm, preferably 0.02 to 0.1 mm, and is preferably suitable for long-term immobilization of enzymes, their activity being maintained. The support is easy to handle, i.e. it can be stored without taking safety precautions. In addition, it has good mechanical and hydrodynamic properties.

To immobilize enzymes, the copolymer is advantageously activated using a diamine and a dialdehyde, preferably glutyraldehyde. In particular, diamines are employed whose terminal amino groups are connected together via alkyl groups or alkylbenzyl groups. Alkyl groups having a chain length of 2, 4 or 6 carbon atoms are particularly preferred. The supports are loaded using an aqueous enzyme solution which expediently contains a buffer, depending on the enzyme type. Lipases can be particularly well immobilized. The buffer is preferably employed in a molarity of 0.05-0.5, particularly 0.1-0.2. The support is incubated in the enzyme solution at room temperature withstirring for 10-20 hours, preferably 14-18 hours. After separating off the aqueous solution, the copolymer can be employed as a biocatalyst.

In the following examples, the invention is described in detail. The percentage data refer to the weight.

EXAMPLE 1

348 ml of petroleum ether (boiling range 100°-140° C.), 175 ml of perchloroethylene and 3.28 g of a polybutadiene oil of molecular weight 1000 to 1500 are placed in a 2 liter 4-necked flask fitted with an anchor stirrer, gas inlet tube, thermometer and reflux condenser, and a solution of 85 g of dimethyldiallylammonium chloride (60% strength aqueous solution), 29.5 g of glycidyl methacrylate, 4.5 g of N-vinylimidazole, 15 g of methylenebisacrylamide in 400 ml of $H_2O$, and 0.57 g of 2,2'-azobis-(2-amidinopropane)dihydrochloride[2,2'-azobis(2-methylpropanimidamide)dihydrochloride, $C_8H_{18}N_6.2HCL$; Chemical Abstracts Registry Number index: 2 977-92-4] is added dropwise over 60 minutes at a stirring speed of 60 rpm. This monomer solution is distributed in the form of fine droplets in the intially introduced organic solution.

The bath is heated to 80° C. within 30 minutes and to 100° C. in a further 40 minutes. The polymerization is then carried out at a bath temperature of 90°-91° C. The $H_2O$ is subsequently removed by azeotropic distillation, and the bead polymer produced is isolated by filtration under suction, washed 2× with 100 ml of acetone, and dried at 60° C. and 200 Torr for 8 hours.

The yield is 95.3 g (95.3% of theory).

A product with the same surface structure is obtained when 15 g of methylenebismethacrylamide are employed in place of the 15 g of methylenebisacrylamide.

EXAMPLE 2

(a)

The procedure according to Example 1 is carried out, but a solution of 85 g of dimethyldiallylammonium chloride (60% strength aqueous solution), 34 g of glycidyl methacrylate, 15 g of methylenebisacrylamide in 400 ml of water, and 0.57 g of 2,2'-azobisacrylamide are added dropwise to the initially introduced organic solution.

The mixture is heated to 80° C. within 30 minutes and polymerized at 75°-80° C.

A yield of 38.5 g of copolymer (98.5% of theory) is obtained.

(b)

The procedure according to Example 2a is carried out, but a solution of 85 g of dimethyldiallylammonium chloride (60% strength aqueous solution), 25 g of glycidyl methacrylate, 9 g of N-vinylimidazole, 15 g of bisacrylamidoacetic acid in 168.4 ml of water, and 0.85 g 2,2'-azobis(2-amidinopropane)dihydrochloride is added dropwise to the initially introduced organic solution, a product thus being obtained of a quality comparable to that of the product of Example 2a.

EXAMPLE 3

The procedure according to Example 1 is carried out, but a solution of 85 g of dimethyldiallylammonium chloride (60% strength aqueous solution), 8.74 g of vinylcyclohexene monooxide, 9 g of N-vinylimidazole, 15 g of methylenebisacrylamide in 350 ml of water, and 0.57 g of 2,2'-azobis-2-(amidinopropane)dihydrochloride is added to the initially introduced organic solution within 60 minutes while passing in nitrogen.

The mixture is heated to a temperature of 85° C., polymerized at 78°–81° C., and subsequently stirred for 30 minutes at 80°–85° C.

A yield of 70.4 g of copolymer (70.9% of theory) is obtained.

EXAMPLE 4

(a)
The procedure according to Example 1 is carried out, but, in place of the polybutadiene polymer, 2.85 g of 1,7-bis(2-hydroxypropyl)-1,1,3,3,5,5,7,7-octamethyltetrasiloxane bisacrylate are added to the initially introduced organic solution. A solution of 85 g of dimethyldiallylammonium chloride (60% strength agueoussolution), 25 g of glycidyl methacrylate, 9 g of N-vinylimidazole, 15 g of methylenebisacrylamide in 400 ml of water, and 0.57 g of 2,2'-azobis(2-amidinopropane)dihydrochloride is added dropwise to the initially introduced organic solution within 60 minutes while passing in nitrogen.

Within a period of 30 minutes, the mixture is heated to 83°–85° C. and polymerized.

A yield of 100 g (100% of theory) is obtained.
(b)
A copolymer of the same quality is obtained when 15 g of polyethylene glycol 600 dimethyacrylate are employed in place of methylenebisacrylamide, and 0.57 g of azobisisobutyronitrile is employed in place of 2,2'-azobis(2-amidinopropane)dihydrochloride.

EXAMPLE 5

(a)
The procedure according to Example 1 is carried out, but, in place of the polybutadiene polymer, a copolymer, which is prepared under a nitrogen atmosphere at 200° C. (Lithene PM4, Rivertex Ltd., GB), of polybutadiene oil and maleic anhydride is initially introduced into the organic solution:

A solution of 85 g of dimethyldiallylammonium chloride (60% strength aqueous solution), 25 g of vinylcyclohexene monooxide, 9 g of vinylimidazole and 15 g of bisacrylamidoacetic acid in 150 ml of water, and 0.57 g of 2,2'-azobis(2-amidinopropane)dihydrochloride is added dropwise to the initially introduced organic solution within 30 minutes while passing in nitrogen.

Within a period of 30 minutes, the mixture is heated to 92° C., polymerized at a temperature of 84°–85° C., and then heated for a further 60 minutes.

A yield of 84.4 g (84.4% of theory) is obtained.
(b)
A copolymer of the same quality is obtained when a solution of 68 g of dimethyldiallylammonium chloride (60% strength aqueous solution), 25 g of glycidyl methacrylate, 9 g of N-vinyl-N-methylacetamide and 19 g of N,N-methylenebisacrylamide in 30 ml of water is added dropwise to the initially introduced organic solution.

EXAMPLE 6

(a)
The procedure according to Example 1 is carried out, but a solution of 85 g of dimethyldiallylammonium chloride (60% strength aqueous solution), 25 g of allyl glycidyl ether, 9 g of N-vinylimidazole and 15 g of methylenebisacrylamide in 350 ml of $H_2O$, and 0.57 g of azoisobutyronitrile is added dropwise to the initially introduced organic solution within 60 minutes while passing in nitrogen.

Over a period of 30 minutes, the mixture is heated to 80° C., polymerized at a temperature of 77°–79° C., and then heated for a further 30 minutes.

68.3 g of copolymer (72% of theory) are obtained.

(b) A product of the same quality is obtained when a solution of 69 g of dimethyldiallyammonium chloride (60% aqueous solution), 25 g of glycidyl methacrylate, 9 g of N-vinylformamide and 15 g of methylenebisacrylamide in 10 ml of water, and 0.456 g of 2,2'-azobis(2-amidinopropane)dihydrochloride is added dropwise to the initially introduced organic solution, and polymerized at 75°–88° C. within 30 minutes.

EXAMPLE 7

The procedure according to Example 1 is carried out, but a solution of 75 g of glycidyl methacrylate, 16.7 g of dimethyldiallylammonium chloride (60% strength aqueous solution) and 15 g of methylenebisacrylamide in 650 ml of of water, and 0.57 g of 2,2'-azobis(2-amidinopropane)dihydrochloride is added dropwise to the initially introduced organic solution within 30 minutes at a stirrer speed of 100 rpm while passing in nitrogen.

Over a period of 30 minutes, the mixture is heated to 90° C. and polymerized at 78°–81° C.

79 g of copolymer (97% of theory) was obtained.

EXAMPLE 8

The procedure according to Example 1 is carried out, but instead of the polybutadiene oil, 3.28 g of 1,7-bis(2-hydroxypropyl)-1,1,3,3,5,5,7,7-octamethyltetrasiloxane bisacrylate are initially introduced into the organic solution. A solution of 85 g of dimethyldiallylammonium chloride (60% strength aqueous solution), 25 g of limonene oxide, 9 g of N-vinylimidazole and 15 g of methylenebisacrylamide in 350 ml of $H_2O$, and 0.57 g of 2,2'-azobis(2-amidinopropane)dihydrochloride is added dropwise to the initially introduced organic solution within 30 minutes at a stirrer speed of 100 rpm while passing in nitrogen.

Over a period of 60 minutes, the mixture is heated to 90° C., polymerized at 75°–76° C., and then heated for a further 30 minutes.

A yield of 73 g of copolymer (73% of theory) is obtained.

EXAMPLE 9

263 ml of perchloroethylene and 14.76 g of a polybutadiene oil are initially introduced into 522 ml of petroleum ether (boiling range 100° to 140° C.) in a 3 liter 4-necked flask fitted with an anchor stirrer, gas inlet tube, thermometer and reflux condenser. A monomer solution of 105 g of glycidyl methacrylate, 7.5 g of N-vinylimidazole, 25 g of diallyldimethylammonium chloride (60% strength aqueous solution) 22.5 g of methylenebisacrylamide in 1050 ml of H$_2$O, and 0.855 g of 2,2'-azobis(2-amidinopropane)dihydrochloride is added through the dropping funnel at a stirrer speed of 120 rpm. During this, this monomer solution is distributed in the form of fine droplets.

Within a period of 30 minutes, the mixture is heated to 90° C. and polymerized at 80°–81° C. The mixture is subsequently stirred for 2 hours, and the H$_2$O is removed by azeotropic distillation over 5 hours. The bead-like copolymer obtained is separated off, washed with acetone, and dried at 50° C. and 266 mbar for 6 hours. 149 g of copolymer (99.3% of theory) are obtained.

EXAMPLE 10

Activation of the Support 4 g of copolymer from Example 1, 4 or 5, 66 ml of dimethoxyethane and 3 g of 1,4-diaminobutane are heated at 80° C. for 3 h. After cooling, the support is filtered off, washed with water until free of amine, and subsequently activated for 1.5 hours at room temperature in a solution of 100 ml of 0.1 molar phosphate buffer (pH 7.0) and 2.4 ml of glutyraldehyde (50% strength aqueous solution). The polymer is separated off and washed with 1 liter of distilled water.

Enzyme fixation 2 g of activated support are stirred for 16 hours at room temperature in 30 ml of 0.1 molar phosphate buffer (pH 7.0) with 200 mg of lipase from *Candida cylindracea* (supplied by Sigma), subsequently filtered off, and washed with distilled water, 0.5 molar sodium chloride solution with 0.1 molar phosphate buffer (pH 7.0). The enzyme activities found are listed in the table below.

EXAMPLE 11

The procedure according to Example 10 is carried out, but, in place of 1,4-diaminobutane, the same amount of 1,6-diaminohexane is employed, and Lipase from *Candida cylindracea* is immobilized on the copolymer from Example 2 or 5. The results are reproduced in the table below.

EXAMPLE 12

2 g of copolymer from Example 1 or 4 are stirred for 16 hours at room temperature in 50 ml of 0.1 molar phosphate buffer (pH 7.5) and 200 mg of lipase from *Candida cylindracea*. The support is separated off and washed successively with water, 0.5 molar sodium chloride solution and again water.

| Fixation of Lipase from *Candida cylindracea*: | | |
|---|---|---|
| Copolymer | Type of fixation | Units/g of support |
| Example 2 | Example 10 | 151 |
| 5 | 10 | 119 |
| 6 | 10 | 151 |
| 5 | 11 | 120 |
| 2 | 11 | 150 |
| 1 | 12 | 92 |
| 4 | 12 | 75 |
| 9 | 11 | 220 |

1 unit of enzyme hydrolizes 1 μmol of carboxylate in one minute.

EXAMPLE 13

Analogously to Example 10, 100 mg of lipase from *Rhizopus Sp.* are immobilized on 2 g of the copolymer from Example 2 or 5. Both fixations display lipase activities of 35 U/g of support.

EXAMPLE 14

200 μl of pigs liver esterase, suspended in 3.2 molar ammonium sulfate solution, are dialyzed for 48 hours at 7° C. against 1 molar phosphate buffer (pH 7.5) before the fixation. The purified enzyme is subsequently fixed, analogously to Example 10, to a copolymer from Example 7. The fixation produces an esterase activity of 15 U/g of support.

EXAMPLE 15

As described in Example 10, lipase from pigs pancreas is fixed to the copolymer from Example 9. The fixation produces a lipase activity of 95 U/g of support.

What we claim is:

1. A crosslinked, porous, bead-like copolymer having
(a) repeating units of the monomeric compound of the formula I,

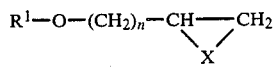

in which
R$^1$ denotes (C$_2$–C$_4$) alkenyl or the corresponding acid,
X denotes oxygen or NH, and
n denotes 1–6,
or repeating units of the compound of the formula II,

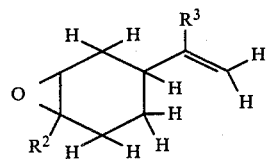

in which
R$^2$ and R$^3$, independently of one another, denote hydrogen or methyl,
or several such compounds,
(b) repeating units of one or more monomeric n-valent crosslinking agents,
(c) repeating units of the monomeric compound of the formula III

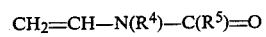

in which
R$^4$ and R$^5$, independently of one another, denote hydrogen or (C$_1$–C$_3$)-alkyl, or, together, represent —(CH$_2$)$_n$— where n=3, 4 or 5,
or several such compounds,
(d) repeating units of the monomeric comopunds of the formula IV,

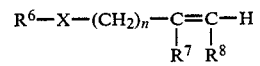

in which
$R^6$ denotes the radical of a heterocyclic 5-membered ring compound which has at least one protonatable nitrogen atom in the ring, or pyridyl, quinolyl, isoquinolyl or pyrazinyl,
$R^7$ and $R^8$ denote hydrogen or $(C_1-C_4)$-alkyl,
X denotes oxygen or sulfur or a direct bond, and n denotes a number from 0 to 4,
or several such compounds,
(e) repeating units of the monomeric compound of the formula V

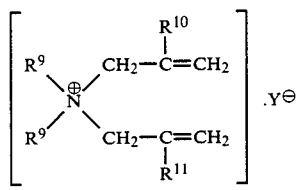

in which
$R^9$ denotes a $(C_1-C_{10})$-alkyl group,
$R^{10}$ and $R^{11}$, independently of one another, denote hydrogen or methyl and
Y denotes halogen,
or several such compounds.

2. The copolymer as claimed in claim 1, wherein the copolymer comprises 10-90% by weight of repeating units of the compound of the formula I or II, 0.05-50% by weight of repeating units of n-valent crosslinking agent, 0-50% by weight or repeating units of the compound of the formula III, 0-90% by weight of repeating units of the compound of the formula IV and 9.5-80% by weight of repeating units of the compound of the formula V.

3. The copolymer is claimed in claim 2, wherein the copolymer comprises 25-75% by weight of repeating units of the compound of the formula I or II, 0.1-35% by weight of repeating units of n-valent crosslinking agent, 5-25% by weight of repeating units of the compound of the formula III, 10-80% by weight of repeating units of the compound of the formula IV and 10-50% by weight of repeating units of the compound of the formula V.

4. The copolymer as claimed in claim 1, wherein it contains, as crosslinking agent, units of N,N'-methylenebisacrylamide and/or N,N'-methylenebismethacrylamide and/or ethylene glycol diacrylate and/or ethylene glycol dimethacrylate and/or diethylene glycol diacrylate and/or diethylene glycol dimethacrylate and/or polyethylene glycol 200 to 600 diacrylate and/or polyethylene glycol 200-600 dimethacrylate and/or N,N',N''-tris(2-acryloyloxyethyl)isocyanurate and/or N,N',N''-tris(2-methacryloyloxyethyl)isocyanurate.

* * * * *